United States Patent [19]

Sauli

[11] 4,099,008

[45] Jul. 4, 1978

[54] PROCESS FOR THE PREPARATION OF 3-(3,5-DICHLOROPHENYL)-HYDANTOIN

[75] Inventor: Michel Sauli, Paris, France

[73] Assignee: Philagro, Lyon, France

[21] Appl. No.: 713,638

[22] Filed: Aug. 12, 1976

[30] Foreign Application Priority Data

Aug. 13, 1975 [FR] France .............................. 75 25209

[51] Int. Cl.$^2$ ........................................... C07D 233/76
[52] U.S. Cl. .................................................. 548/314
[58] Field of Search ...................... 260/209.5; 542/314

[56] References Cited

U.S. PATENT DOCUMENTS

| 3,389,146 | 6/1968 | Kitasaki et al. ................... 260/309.5 |
| 3,395,153 | 7/1968 | Kitasaki et al. ................... 260/309.5 |
| 3,448,116 | 6/1969 | McCaully et al. ................. 260/309.5 |
| 3,668,217 | 6/1972 | Fujinami et al. .................. 260/309.5 |
| 3,676,456 | 7/1972 | Gruenfeld .......................... 260/309.5 |
| 3,684,774 | 8/1972 | Merten et al. ..................... 260/309.5 |
| 3,814,776 | 6/1974 | Fischer et al. .................... 260/309.5 |

*Primary Examiner*—Natalie Trousof
*Attorney, Agent, or Firm*—Browdy and Neimark

[57] ABSTRACT

A process for the manufacture of 3-(3,5-dichlorophenyl)-hydantoin comprises cyclizing 3-(3,5-dichlorophenyl)-ureidoacetic acid in the presence of a catalytic amount relative to the ureidoacetic acid of an acid dehydrating agent and in the presence of an organic solvent which forms an azeotrope with water; the water formed during the reaction is eliminated by azeotropic distillation.

7 Claims, No Drawings

PROCESS FOR THE PREPARATION OF 3-(3,5-DICHLOROPHENYL)-HYDANTOIN

The present invention relates to a new process for the preparation of 3-(3,5-dichlorophenyl)-hydantoin, which is particularly useful as an intermediate in the preparation of 1-isopropylcarbamoyl-3-(3,5-dichlorophenyl)-hydantoin.

1-Isopropylcarbamoyl-3-(3,5-dichlorophenyl)-hydantoin, which possesses remarkable fungicidal properties, forms the subject of French Pat. No. 70/28,084 published under No. 2,120,222.

According to French Patent 69/39,612 published under No. 2,024,141, 3-(3,5-dichlorophenyl)-hydantoin can be obtained by intramolecular cyclization, at an elevated temperature, in the presence of an acid catalyst, of a urea derivative of the general formula

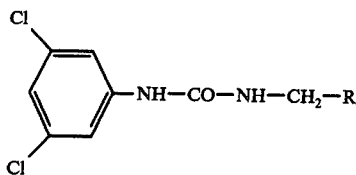

(I)

in which R represents a carboxyl or cyano radical.

In general, the cyclisation is effected by heating the urea derivative of the general formula (I) under reflux in a dilute inorganic acid, such as hydrochloric acid, in particular 20% strength hydrochloric acid, sulphuric acid or phosphoric acid.

There has now been found, and it is this which forms the subject of the present invention, a process for the manufacture of 3-(3,5-dichlorophenyl)-hydantoin by cyclising 3-(3,5-dichlorophenyl)-ureidoacetic acid in the presence of an acid, characterised in that the acid is a dehydrating agent used in a catalytic amount relative to the ureidoacetic acid starting material, that the reaction is carried out in an organic solvent which forms an azeotrope with water and that the water formed during the reaction is eliminated by azeotropic distillation.

By dehydrating agent there is essentially understood sulphuric acid, methanesulphonic acid and benzenesulphonic acid.

By catalytic amount, there is understood an amount markedly less than the stoichiometric amount. This amount is preferably at most equal to half the stoichiometric amount and at least equal to 0.05 mol/mol of ureidoacetic acid. The reaction is brought about with excellent yield using upwards of 0.1 mol of dehydrating agent per mol of ureidoacetic acid.

Amounts less than 0.05 mol give insufficient yields whilst amounts greater than 0.1 mol and, a fortiori, greater than 0.5 mol do not produce an improvement and are detrimental to the economical character of the process.

Furthermore, the organic solvent used must give an azeotrope with the water produced from the cyclization. As solvents of this type, there may be mentioned benzene, the chlorobenzenes, toluene and xylene, chlorobenzene being preferred.

The reaction is complete when the reaction mixture becomes limpid.

The 3-(3,5-dichlorophenyl)-hydantoin thus obtained is isolated by filtration after cooling the reaction mixture.

The examples which follow and are given without implying a limitation show how the invention can be put into practice.

EXAMPLE 1 (sulphuric acid)

To a suspension of 3-(3,5-dichlorophenyl)-ureidoacetic acid (813 g.) in chlorobenzene (3,500 cc.) is added concentrated sulphuric acid ($d = 1.83$) (16 cc.), representing 0.095 mol per mol of ureidoacetic acid. The water formed in the reaction is removed by azeotropic distillation. After 45 minutes' distillation, a limpid solution is obtained. After cooling to about 15° C, the precipitate formed is filtered off and washed on the filter with ethanol (500 cc.) at 10° C. After drying, 3-(3,5-dichlorophenyl)-hydantoin (724 g.) melting at 199° C is obtained. Yield: 95.4%.

3-(3,5-Dichlorophenyl)-ureidoacetic acid, melting at 230° C and used as the starting material, is obtained by the action of 3,5-dichlorophenyl isocyanate on the sodium salt of glycine in solution in water.

EXAMPLE 2 (methanesulphonic acid)

To a suspension of 3-(3,5-dichlorophenyl)-ureidoacetic acid (526 g.) in chlorobenzene (2,250 cc.) is added methanesulphonic acid ($d = 1.48$) (10 cc., representing 0.077 mol per mol of ureidoacetic acid). The water formed in the reaction is removed by azeotropic distillation. After 45 minutes' distillation, a limpid solution is obtained. After cooling to about 15° C, the precipitate formed is filtered off and washed on the filter with ethanol (500 cc.) at 10° C. After drying, 3-(3,5-dichlorophenyl)-hydantoin (467 g.) melting at 199° C is obtained. Yield: 94%.

EXAMPLE 3 (benzenesulphonic acid)

To a suspension of 3-(3,5-dichlorophenyl)-ureidoacetic acid (26.3 g.) in chlorobenzene (180 cc.) is added benzenesulphonic acid (1.2 g. representing 0.068 mol per mol of ureidoacetic acid). The water formed in the reaction is removed by azeotropic distillation. After 30 minutes' distillation, a limpid solution is obtained. After cooling to about 15° C, the precipitate formed is filtered off and washed on the filter with ethanol (25 cc.) at 10° C. After drying, 3-(3,5-dichlorophenyl)-hydantoin (22.2 g.) melting at 199° C is obtained. Yield: 90.5%.

I claim:

1. In a process for the preparation of 3-(3,5-dichlorophenyl)-hydantoin by cyclizing 3-(3,5-dichlorophenyl)-ureidoacetic acid in the presence of an acid the improvement wherein, the acid is a dehydrating agent which is used in a catalytic amount less than stoichiometric relative to the ureidoacetic acid starting material, and the reaction is carried out in a sufficient amount of an organic solvent reaction medium which forms an azeotrope with water, whereby the water formed during the reaction is eliminated by azeotropic distillation and wherein on completion of the reaction, the reaction mixture becomes limpid.

2. A process according to claim 1, wherein the organic solvent is chlorobenzene.

3. A process according to claim 1, wherein the dehydrating agent is sulphuric acid, methanesulphonic acid or benzenesulphonic acid.

4. Process according to claim 1, wherein the dehydrating agent is used at the rate of 0.05 to 0.5 mol per mol of 3-(3,5-dichlorophenyl)-ureidoacetic acid.

5. A process according to claim 4, wherein about 0.1 mol of dehydrating agent is used per mol of 3-(3,5-dichlorophenyl)-ureidoacetic acid.

6. A process in accordance with claim 1 wherein the organic solvent reaction medium consists essentially of benzene, a chlorobenzene, toluene or xylene.

7. A process in accordance with claim 1 wherein the organic solvent is chlorobenzene, the dehydrating agent is sulphuric acid, methanesulphonic acid or benzenesulphonic acid, and the dehydrating agent is present in an amount of 0.05 to about 0.1 mols per mol of 3-(3,5-dichloro-phenyl)-ureidoacetic acid.

* * * * *